United States Patent
Shigetou et al.

(12) 
(10) Patent No.: US 6,303,759 B1
(45) Date of Patent: *Oct. 16, 2001

(54) DYE-LABELED AND POLYMERIZED ANTIBODY AND METHOD FOR PREPARING THE SAME

(75) Inventors: Nobuyuki Shigetou, Hirakata; Jinsei Miyazaki, Higashiosaka; Mahito Hirai, Hirakata, all of (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/310,850

(22) Filed: May 13, 1999

Related U.S. Application Data

(63) Continuation-in-part of application No. 08/831,204, filed on Apr. 2, 1997, now Pat. No. 5,922,618, and a continuation-in-part of application No. 08/745,337, filed on Nov. 8, 1996, now Pat. No. 5,965,713.

(30) Foreign Application Priority Data

May 14, 1998 (JP) .................................... 10-132420

(51) Int. Cl.[7] .............................. C07K 17/02; C07K 1/13; G01N 33/533
(52) U.S. Cl. ................... 530/391.5; 436/800; 530/391.3
(58) Field of Search .............................. 530/391.3, 391.5; 436/800

(56) References Cited

U.S. PATENT DOCUMENTS

| 4,153,417 | 5/1979 | Hallgren et al. . | |
|---|---|---|---|
| 5,650,334 | 7/1997 | Zuk et al. . | |
| 5,714,386 | 2/1998 | Roederer . | |
| 5,965,713 | * 10/1999 | Shigeto et al. | 530/402 |

FOREIGN PATENT DOCUMENTS

| 0800083 | 8/1997 | (EP) . |
|---|---|---|
| 08259826 A | * 10/1996 | (JP) . |
| 09132725 | 5/1997 | (JP) . |
| 94/03631 | 2/1994 | (WO) . |
| 95/06483 | 9/1995 | (WO) . |

OTHER PUBLICATIONS

Bajyanason et al, Derwent–Acc–No.: 1990–224610.*

Spector, D.L., "Floursecent labeling of antibodies and DNA probes" 1998, Cold Spring Harbour Laboratory Press, vol. 2 of "Cells: a Laboratory Manual"; "Light Microscopy and Cell Structure" pp. 82.1–82.7, table 82.1.

Mujumdar, R B, et al. "Cyanine Dye Labeling Reagents: sulfoindocyanine Succinimidyl Esters" Bioconjugate Chemistry, US, American Chemical Society, Washington, vol. 4, No. 2 pp. 105–111.

* cited by examiner

*Primary Examiner*—Mary E. Ceperley
(74) *Attorney, Agent, or Firm*—McDermott, Will & Emery

(57) ABSTRACT

The present invention provides a highly sensitive dye-labeled and polymerized antibody that can detect a target substance even when the target substance has a low concentration. The dye-labeled and polymerized antibody of the present invention comprises a polymerized antibody, which has been polymerized with a polyfunctional reagent, and a cyanine dye for labeling the polymerized antibody represented by the formula (1) given below:

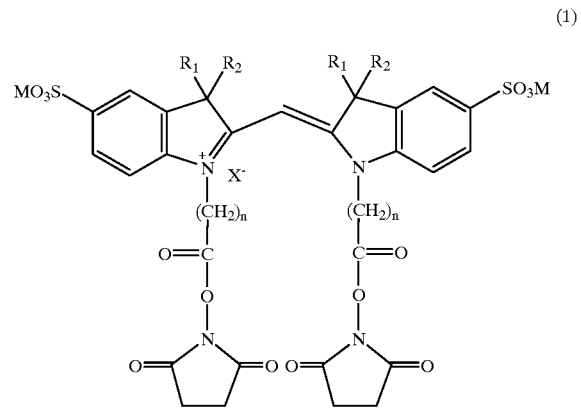

where $R_1$ and $R_2$ denote hydrogen or an alkyl group, X denotes a halogen, M denotes hydrogen or an alkali metal, and n represents an integer in a range of 1 to 4.

3 Claims, 1 Drawing Sheet

DYE-LABELED AND POLYMERIZED ANTIBODY AND METHOD FOR PREPARING THE SAME

CROSS-REFERENCE TO RELATED APPLICATIONS

This application is a continuation-in-part of application Ser. No. 08/831,204 filed Apr. 2, 1997, now U.S. Pat. No. 5,922,618, and a continuation-in-part of application Ser. No. 08/745,337 filed Nov. 8, 1996, now U.S. Pat. No. 5,965,713.

BACKGROUND OF THE INVENTION

The present invention relates to a polymerized antibody labeled with a cyanine dye and a method for preparing the same.

The dye-labeled antibody prepared by labeling an antibody with a dye specifically reacts with an antigen included in a sample solution and is readily recognizable with naked eyes. The dye-labeled antibodies are accordingly applied for immunosensors, each of which takes advantage of an immunological antigen-antibody reaction to detect a target substance included in a sample solution, and are used for diagnoses in a variety of medical institutions.

Cyanine dyes having the high molar absorption coefficient and the high reactivity are often used to label antibodies (Bioconjugate Chemistry Vol. 4, No. 2, pp105–111, 1993).

The functional group of the cyanine dye reacts with and is covalently bound to an amino group or a carboxyl group included in an antibody, and 20 to 50 molecules of the dye are attached to one molecule of the antibody.

The cyanine dye-labeled antibody thus prepared generally has high visual recognizability, and is effectively applied for, for example, immunochromatography to detect a small amount of a specific substance, such as human chorionic gonadotropin (HCG) that is present only in the urine of pregnant women.

One molecule of the antibody generally has only two sites reacting with the antigen and thereby has relatively low reaction sensitivity to the antigen.

When the conventional dye-labeled antigen is used for an immunosensor, the immunosensor accordingly does not have sufficient sensitivity. In the case that the sample solution contains a low concentration of a target substance (antigen), it is difficult to detect the target substance.

BRIEF SUMMARY OF THE INVENTION

The object of the present invention is thus to provide a highly sensitive dye-labeled and polymerized antibody that enables detection of even a low concentration of a target substance.

Another object of the present invention is to provide a method for preparing such a dye-labeled and polymerized antibody.

The present invention provides a dye-labeled and polymerized antibody comprising an antibody and a cyanine dye represented by the formula (1) given below:

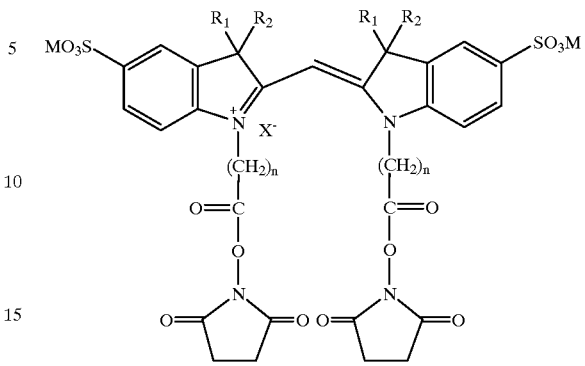

(1)

where $R_1$ and $R_2$ denote hydrogen or an alkyl group, X denotes a halogen, M denotes hydrogen or an alkali metal, and n represents an integer in a range of 1 to 4, wherein the antibody is polymerized via a polyfunctional reagent and the polymerized antibody is labeled with the cyanine dye.

The polymerized antibody is a polyvalent antibody having a large number of sites reacting with an antigen and thereby has a higher binding sensitivity to the antigen, compared with the conventional divalent antibody.

The number of dye molecules bound to one molecule of the polymerized antibody is greater than the number of dye molecules bound to one molecule of the conventional antibody. This improves the visual recognizability.

When the dye-labeled and polymerized antibody of the present invention is applied for, for example, immunochromatography, the immunochromatography can detect a target substance (sample) with high sensitivity even when the sample has a low concentration. Because of the high sensitivity, the dye-labeled and polymerized antibody of the present invention is applicable for biosensors.

In accordance with one preferable application of the dye-labeled and polymerized antibody of the present invention, a skeleton of the cyanine dye is bound to the polymerized antibody via a covalent bond between an acyl carbon originated from a succinimidyl group in the cyanine dye and a nitrogen originated from an amino group in the polymerized antibody.

The degree of polymerization of antibody in the dye-labeled and polymerized antibody of the present invention is generally in a range of 2 to 50.

The present invention is also directed to a method for preparing a dye-labeled and polymerized antibody. The method includes the steps of: polymerizing an antibody using a polyfunctional reagent in a neutral or a weak alkaline phosphate buffer solution; and adding a cyanine dye represented by the formula (1) given above to the buffer solution, so as to label the polymerized antibody. It is here preferable that the phosphate buffer solution has a pH value in a range of 7.0 to 8.0.

The antibody used to prepare the dye-labeled and polymerized antibody of the present invention is not specifically restricted, but may have a variety of origins and sub-classes. Available examples of the antibody include immunoglobulins (Ig), such as mouse IgG, mouse IgM, mouse IgA, mouse IgE, rat IgG, rat IgM, rat IgA, rat IgE, rabbit IgG, rabbit IgM, rabbit IgA, rabbit IgE, goat IgG, goat IgM, goat IgE, goat IgA. sheep IgG, sheep IgM, sheep IgA, and sheep IgE. These antibodies may be of commercial origin or directly collected from the corresponding animals.

The polyfunctional reagent used in the present invention has two or more functional groups (for example, succinimidyl group, pyridyldisulfide group), which can be linked with an antibody, in one identical molecule. Available examples of the polyfunctional reagent include dithiobis (sulfosuccinimidyl propionate) represented by the formula (2), bis (sulfosuccinimidyl) suberate represented by the formula (3), disuccinimidyl tartrate represented by the formula (4), ethylene glycol bis(succinimidyl succinate) represented by the formula (5), and N-succinimidyl-3-(2-pyridyldithio) propionate represented by the formula (6).

(2)

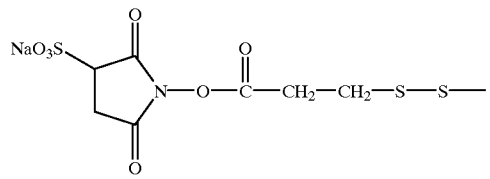
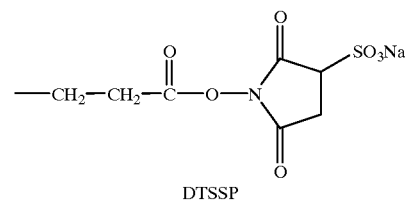

DTSSP (3)

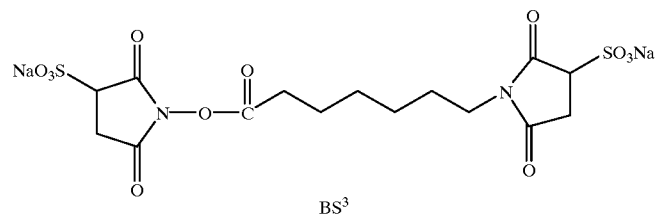

BS³

(4)

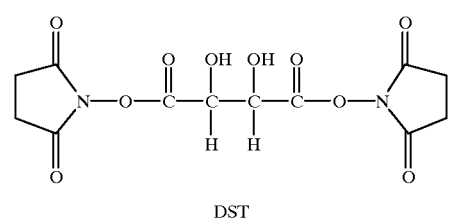

DST (5)

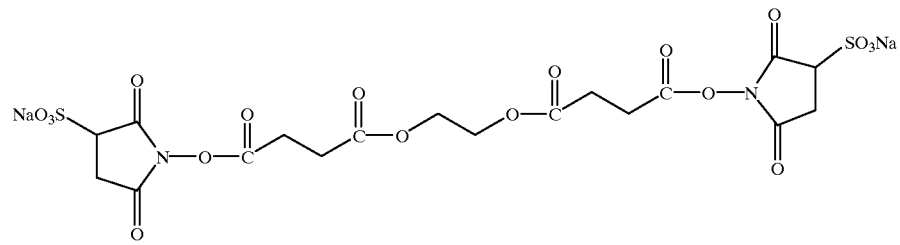

EGS (6)

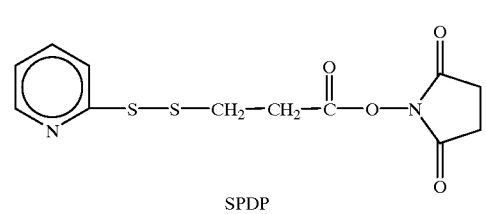

SPDP

The cyanine dye represented by the formula (1) is a red dye readily recognizable with naked eyes. The cyanine dye has a less number of conjugated carbons and thereby has the highest solubility in water among a variety of cyanine dyes.

The halogen represented by X in the formula (1) may be fluorine, chlorine, bromine, or iodine. The metal represented by M may be lithium, sodium, or potassium.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
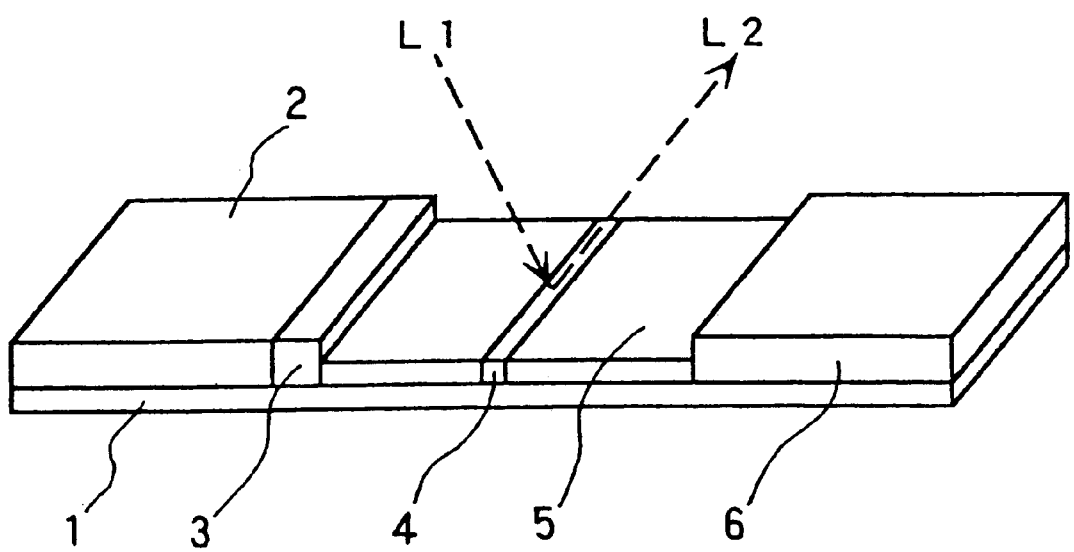
FIG. 1 is a perspective view schematically illustrating the structure of an immunochromatography sensor as an example of the present invention.

The following describes one exemplified process of synthesizing the cyanine dye represented by the formula (1) given above.

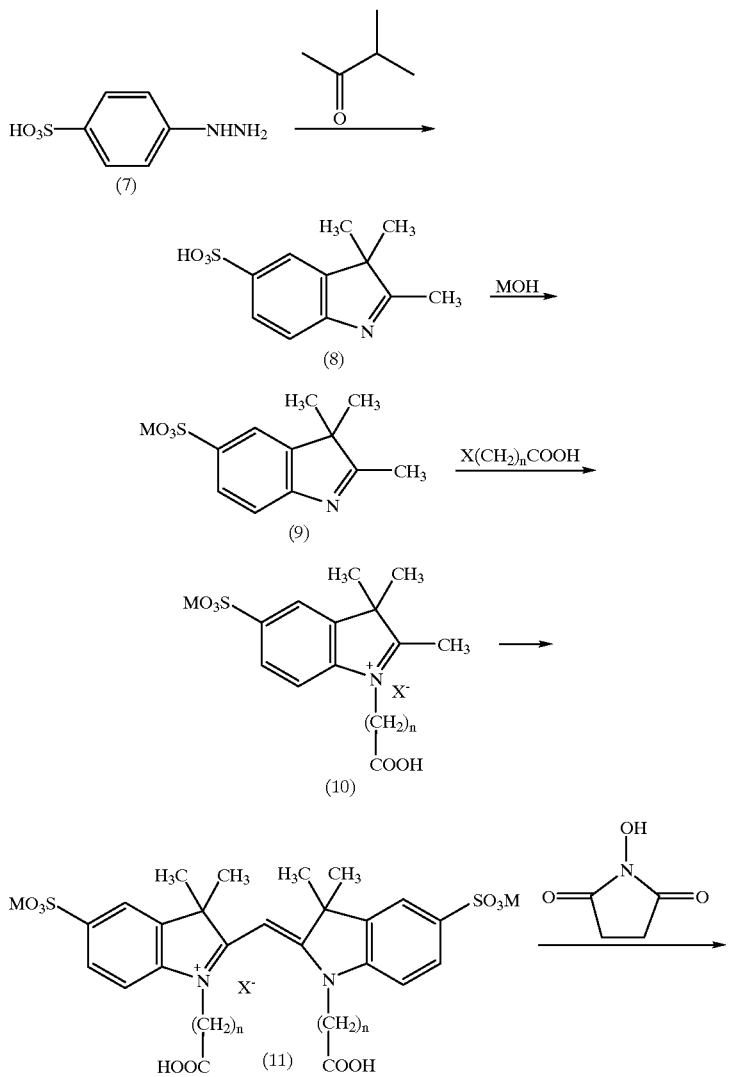

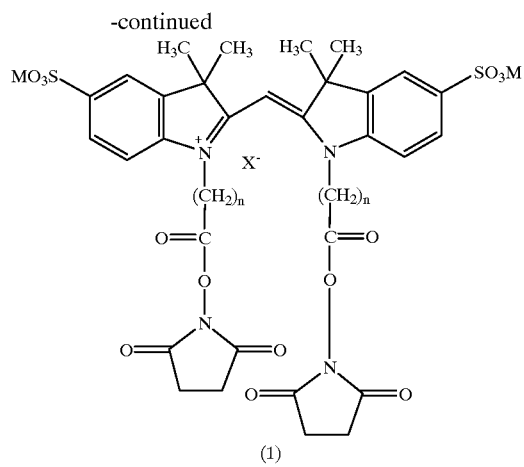

(1)

The process first dissolves hydrazinobenzenesulfonic acid (7) and isopropyl methyl ketone in an acidic solvent and heats the mixture to obtain indoleniumsulfonate (8). The process then adds a metal hydroxide-saturated alcohol solution into an alcohol solution of indoleniumsulfonate (8), so as to yield a metal salt of indoleniumsulfonate (9).

The process subsequently adds a halogenized fatty acid to an organic solvent solution of the metal salt (9) and heats the mixture to obtain a metal salt of carboxyalkylindoleniumsulfonate (10). By taking into account the solubility in water, it is preferable that the halogenized fatty acid has one to four carbon atoms.

The process then dissolves the metal salt (10) and N-carboxyethyl-3,3-dimethylindolenine into a basic organic solvent and heats the mixture to prepare a carboxylic acid derivative (11). The process subsequently adds hydroxysuccinimide and dicyclohexylcarbodiimide as a condensing agent to the organic solvent solution of the carboxylic acid derivative (11) and well stirs the mixture to yield the cyanine dye represented by the formula (1).

The halogen included in the respective compounds represented by the formula (1), the formula (10), and the formula (11) may be fluorine, chlorine, bromine, or iodine. The metal included in the respective compounds represented by the formula (1) and the formulae (9) through (11) may be lithium, sodium, or potassium.

The following describes the mechanism of polymerization reaction of the antibody with the polyfunctional reagent.

(12)

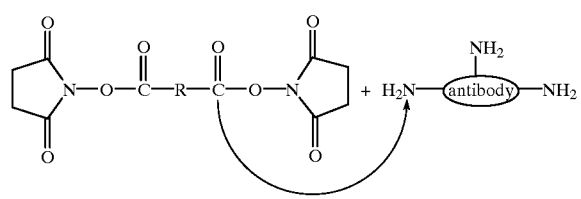

(13)

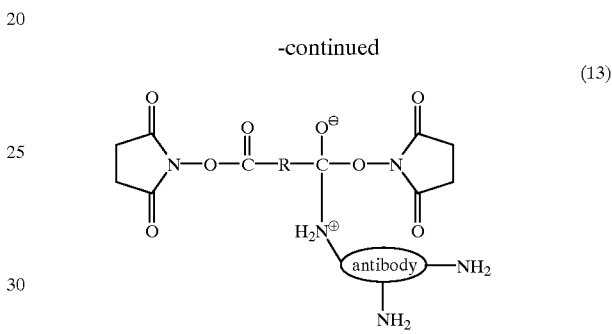

(14)

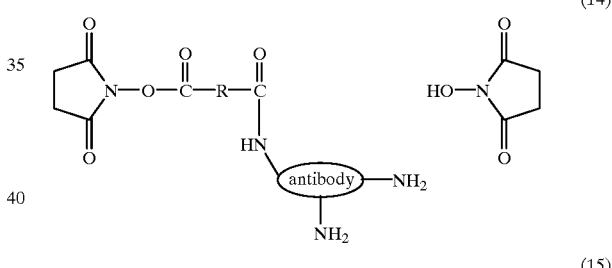

(15)

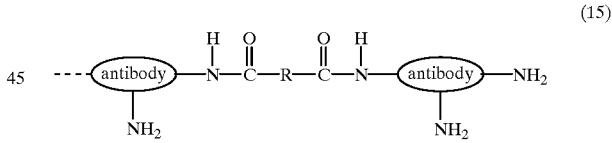

When the antibody is mixed with the polyfunctional reagent (dithiobis(sulfosuccinimidyl propionate) having two or more succinimidyl groups) as shown by the formula (12), an amino group in the antibody approaches an ester bond of one succinimidyl group in the reagent as shown by the formula (13).

The amino group reacts with the ester bond as shown by the formula (14), so that one hydrogen atom is released from the amino group. The hydrogen atom released from the amino group is attached to succinimide in the succinimidyl group. Succinimide is then changed to hydroxysuccinimide, which is released from the succinimidyl group. At the same time, the residue of the succinimidyl group and the hydrogen atom-released amino group combine to form an amide bond, through which the reagent is linked with the antibody.

The other succinimidyl groups in the reagent are subjected to the similar reaction, so that the reagent is bound to other antibodies through the amide bond as shown by the formula (15). This reaction is repeated to polymerize the antibody.

The succinimidyl group in the cyanine dye is bound to the amino group in the antibody according to the same mechanism as discussed above.

The present invention is described more in detail with a concrete example.

(1) Polymerization of Mouse IgG

The polymerization process first dissolved 10 mg (6.667×$10^{-5}$ mmol) of mouse IgG (hereinafter simply referred to as IgG) into 1 ml of a phosphate buffer solution (hereinafter referred to as PBS). The process then added dropwise 0.1 ml of a PBS solution of dithiobis(sulfosuccinimidyl propionate) (manufactured by Pierce Corp., hereinafter referred to as DTSSP) with stirring at room temperature. The PBS solution of DTSSP added dropwise contained 4.057 mg (0.006667 mmol, 100 equivalents) of DTSSP.

After stirring the mixed solution at 35° C. for 30 minutes, the process filtered the mixed solution through a Sepharose gel (manufactured by Pharmacia Fine Chemical Inc., Sephadex G25M column). This gave approximately 6 ml of the PBS solution containing IgG aggregate (hereinafter referred to as IgGagg.). The concentration of the PBS solution thus obtained was determined by the procedure discussed below.

The procedure collected 0.5 ml of the PBS solution and measured the absorbance at 280 nm. The observed absorbance was 2.43. The absorbance at 280 nm is attributed to IgG, so that the concentration [IgGagg.] of IgG molecules in the IgG aggregate is determined according to the following equation. Here the molar absorption coefficient of IgG at 280 nm is set equal to 2.099×$10^5$.

$$[\text{IgGagg.}] = 2.43/2.099 \times 10^5 = 1.158 \times 10^{-5} (M)$$

(2) Labeling Polymerized Antibody with Dye

The process dissolved the cyanine dye represented by the formula (1) into 0.2 ml of the PBS (400 equivalents of the total protein quantity) to obtain 26.8 mg of a dye solution (hereinafter referred to as SLIC1). The cyanine dye included iodine as X, potassium as M, and 2 carbon atoms as n in the formula (1)

The process slowly added the SLIC1 dropwise to the IgGagg. solution (total amount of antibody: 10 mg) obtained in the process (1). After the mixed solution was stood still at 4° C. for 20 hours, the process dialyzed the mixed solution against 20 liters of a PBS solution containing sodium azide as an antiseptics, in order to remove unreacted dye molecules. This gave approximately 6 ml of the PBS solution containing SLIC1-labeled polymerized antibody.

The number of SLIC1 molecules per one IgG molecule in the SLIC1-labeled polymerized antibody was determined according to the following procedure.

The observed absorbance of the resultant solution was 6.80 at 280 nm and 40.2 at 430 nm. The polymerized antibody does not have absorption at 430 nm, so that the observed absorbance at 430 nm is attributed to SLIC1. The concentration [SLIC1] of the SLIC1 is thus determined by the following equation. Here the molar absorption coefficient of SLIC1 at 430 nm is set equal to 1×$10^5$.

$$[\text{SLIC1}] = 40.2/1 \times 10^5 = 4.02 \times 10^{-4} (M)$$

The observed absorbance at 280 nm is originated from IgG of the polymerized antibody. The bound SLIC1, however, also has absorption at 280 nm. The concentration [IgGagg.] of the IgG molecules in the polymerized antibody is accordingly determined by subtracting the effect of this absorption. Here $Ab_{280\_IgG}$ represents the absorbance attributed to the polymerized antibody at 280 nm, the molar absorption coefficient of SLIC1 at 280 nm is set equal to 9.8×$10^3$, and the molar absorption coefficient of the IgG molecules in the polymerized antibody at 280 nm is 2.099×$10^5$.

$$Ab_{280\_IgG} = 6.8 - (4.02 \times 10^{-4} \times 9.8 \times 10^3) = 2.86$$

$$[\text{IgGagg.}] = 2.86/2.099 \times 10^5 = 1.363 \times 10^{-5} (M)$$

The number of SLIC1 molecules bound to one IgG molecule in the SLIC1-labeled polymerized antibody is accordingly given by:

$$[\text{SLIC1}]/[\text{IgGagg.}] = 4.02 \times 10^{-4}/1.363 \times 10^{-5} = 29.5$$

(3) Evaluation of Dye-Labeled and Polymerized Antibody

The dye-labeled and polymerized antibody obtained in the process (2) was applied for an immunochromatography sensor. The luminescence due to aggregation of the dye-labeled and polymerized antibody was determined by measuring the absorbance at 430 nm.

FIG. 1 is a perspective view schematically illustrating the structure of the immunochromatography sensor. A first glass filter 2, a nitrocellulose antibody fixation film 5, and a second glass filter 6 are arranged in this sequence on a plate base 1 made of plastics, such as poly(vinyl chloride). One end of the first glass filter 2 that is in contact with the antibody fixation film 5 is impregnated with the dye-labeled and polymerized antibody obtained in the process (2). This end forms a labeled antibody section 3. An antibody that reacts with the same antigen as the dye-labeled and polymerized antibody is fixed by adsorption on a predetermined area of the antibody fixation film 5. This area forms an antibody fixation section 4.

The absorbance is measured by the following procedure with the immunochromatography sensor having the above structure.

Referring to FIG. 1, when a sample solution is added dropwise to the other end of the first glass filter 2 that is not in contact with the antibody fixation film 5, the sample solution moves from the first glass filter 2 towards the second glass filter 6 based on the principle of chromatography. On the labeled antibody section 3, the dye-labeled and polymerized antibody is bound to the antigen included in the sample solution. The sample solution containing the antigen bound to the labeled antibody then moves to the antibody fixation section 4, where the antigen is bound to the fixation antibody and fixed. The remaining sample solution continues moving across the antibody fixation film 5 and is eventually absorbed by the second glass filter 6.

The absorbance was determined by irradiating the antibody fixation section 4 with light (L1) having the wavelength of 430 nm and measuring reflected light L2.

A dye-labeled antibody of comparative example was prepared in the same manner as above, except the polymerization of the antibody. The dye-labeled antibody of comparative example was also applied for immunochromatography sensor, and the absorbance was determined by the above procedure.

The absorbance of the dye-labeled and polymerized antibody of the present invention was about 0.8, whereas the absorbance of the dye-labeled antibody of comparative example was about 0.07.

This result clearly shows that the sensitivity of the dye-labeled and polymerized antibody of the present invention is approximately 10 times the sensitivity of the comparative example.

As described above, the dye-labeled and polymerized antibody of the present invention has a large number of reaction sites with an antigen and thereby has high sensitivity to the antigen. The dye-labeled and polymerized antibody of the present invention is, for example, effectively applied for immunochromatographysensor. This sensor has the significantly higher sensitivity than that of a sensor with a labeled antibody prepared by the conventional method.

Although the present invention has been described in terms of the presently preferred embodiments, It is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A dye-labeled and polymerized antibody comprising an antibody and a cyanine dye represented by the following formula (1):

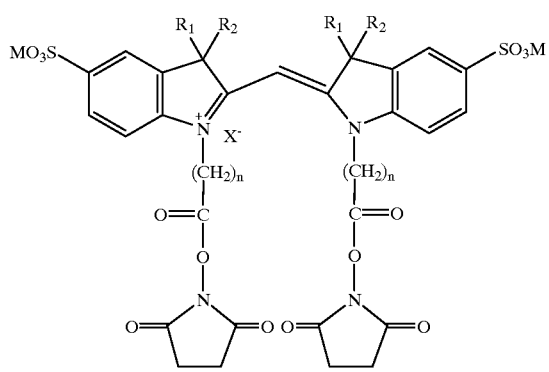

where $R_1$ and $R_2$ denote hydrogen or an alkyl group, X denotes a halogen, M denotes hydrogen or an alkali metal, and n represents an integer in a range of 1 to 4, wherein said antibody is polymerized via a polyfunctional reagent and the polymerized antibody is labeled with said cyanine dye.

2. The dye-labeled and polymerized antibody in accordance with claim 1, wherein a skeleton of said cyanine dye is bound to said polymerized antibody via a covalent bond between an acyl carbon originated from a succinimidyl group in said cyanine dye and a nitrogen originated from an amino group in said polymerized antibody.

3. A method for preparing a dye-labeled and polymerized antibody, said method comprising the steps of:

polymerizing an antibody using a polyfunctional reagent in a neutral or a weak alkaline phosphate buffer solution; and adding a cyanine dye represented by the following formula (1) to said buffer solution to label the polymerized antibody:

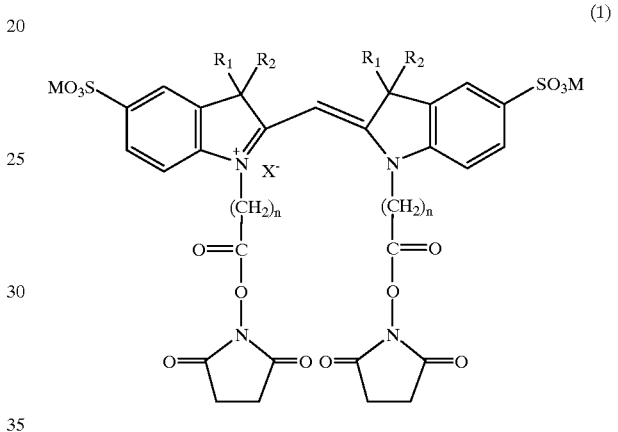

where $R_1$ and $R_2$ denote hydrogen or an alkyl group, X denotes a halogen, M denotes hydrogen or an alkali metal, and n represents an integer in a range of 1 to 4.

* * * * *